US012808842B2

(12) United States Patent
Nakagawa et al.

(10) Patent No.: US 12,808,842 B2
(45) Date of Patent: Nov. 24, 2026

(54) GAS DETECTION APPARATUS AND GAS DETECTION SYSTEM

(71) Applicant: KYOCERA Corporation, Kyoto (JP)

(72) Inventors: Emiko Nakagawa, Kyoto (JP); Shinnosuke Nakamura, Kyoto (JP); Daisuke Ueyama, Kyoto (JP)

(73) Assignee: KYOCERA Corporation, Kyoto (JP)

( * ) Notice: Subject to any disclaimer, the term of this patent is extended or adjusted under 35 U.S.C. 154(b) by 167 days.

(21) Appl. No.: 18/833,296

(22) PCT Filed: Jan. 16, 2023

(86) PCT No.: PCT/JP2023/000913
§ 371 (c)(1),
(2) Date: Jul. 25, 2024

(87) PCT Pub. No.: WO2023/145501
PCT Pub. Date: Aug. 3, 2023

(65) Prior Publication Data

US 2025/0102461 A1 Mar. 27, 2025

(30) Foreign Application Priority Data

Jan. 27, 2022 (JP) ................................ 2022-011291

(51) Int. Cl.
*G01N 27/416* (2006.01)
*G01N 33/00* (2006.01)

(52) U.S. Cl.
CPC ....... *G01N 27/416* (2013.01); *G01N 33/0044* (2013.01); *G01N 33/0047* (2013.01)

(58) Field of Classification Search
CPC .. G01N 27/12; G01N 27/416; G01N 33/0031; G01N 33/0044; G01N 33/0047; G01N 33/483; G01N 33/497
See application file for complete search history.

(56) References Cited

U.S. PATENT DOCUMENTS

2016/0220170 A1 8/2016 Hasegawa et al.
2017/0089875 A1 3/2017 Hasegawa et al.
2017/0370936 A1 12/2017 Hasegawa et al.
2020/0072816 A1* 3/2020 Momose ............ G01N 33/0044
2020/0150122 A1 5/2020 Hasegawa et al.
(Continued)

FOREIGN PATENT DOCUMENTS

JP 2005-189146 A 7/2005
JP 2009-250922 A 10/2009
(Continued)

*Primary Examiner* — Gurpreet Kaur
(74) *Attorney, Agent, or Firm* — Procopio, Cory, Hargreaves & Savitch LLP

(57) ABSTRACT

The concentration of a component in sample gas is accurately detected. A gas detection apparatus includes a collector, a first gas sensor, and a second gas sensor. The collector collects sample gas including first detected gas and second detected gas. Each of the first gas sensor and the second gas sensor is a gas sensor capable of detecting both the first detected gas and the second detected gas. The first gas sensor and the second gas sensor are different from each other in the relative relationship between the detection sensitivity to the first detected gas and the detection sensitivity for the second detected gas.

10 Claims, 8 Drawing Sheets

(56) References Cited

U.S. PATENT DOCUMENTS

| | | | | |
|---|---|---|---|---|
| 2022/0170873 | A1* | 6/2022 | Abe | G01N 33/0004 |
| 2023/0012942 | A1 | 1/2023 | Abe | |

FOREIGN PATENT DOCUMENTS

| | | | |
|---|---|---|---|
| JP | 2015-068820 | A | 4/2015 |
| JP | 2016-145809 | A | 8/2016 |
| JP | 2017-067538 | A | 4/2017 |
| JP | 2021-067548 | A | 4/2021 |
| WO | 2020/189785 | A1 | 9/2020 |
| WO | 2021-117691 | A1 | 6/2021 |

* cited by examiner

GAS DETECTION APPARATUS AND GAS DETECTION SYSTEM

TECHNICAL FIELD

The present disclosure relates to a gas detection apparatus that detects a gas concentration, and a gas detection system including the gas detection apparatus.

BACKGROUND OF INVENTION

A system that detects odorous gas emitted from feces discharged by an examinee has been known (Patent Document 1 for example).

CITATION LIST

Patent Literature

Patent Document 1: JP 2016-145809 A

SUMMARY

A gas detection apparatus according to an aspect of the present disclosure includes: a sample gas collector configured to collect sample gas including first detected gas and second detected gas; and a gas detector including a plurality of gas sensors including a first gas sensor and a second gas sensor capable of detecting both the first detected gas and the second detected gas in the sample gas, wherein the first gas sensor and the second gas sensor are different from each other in relative relationship between detection sensitivity to the first detected gas and detection sensitivity to the second detected gas.

DESCRIPTION OF EMBODIMENTS

First Embodiment

One embodiment of the present disclosure will be described in detail below.

<Analysis System 100>

Figure 1:
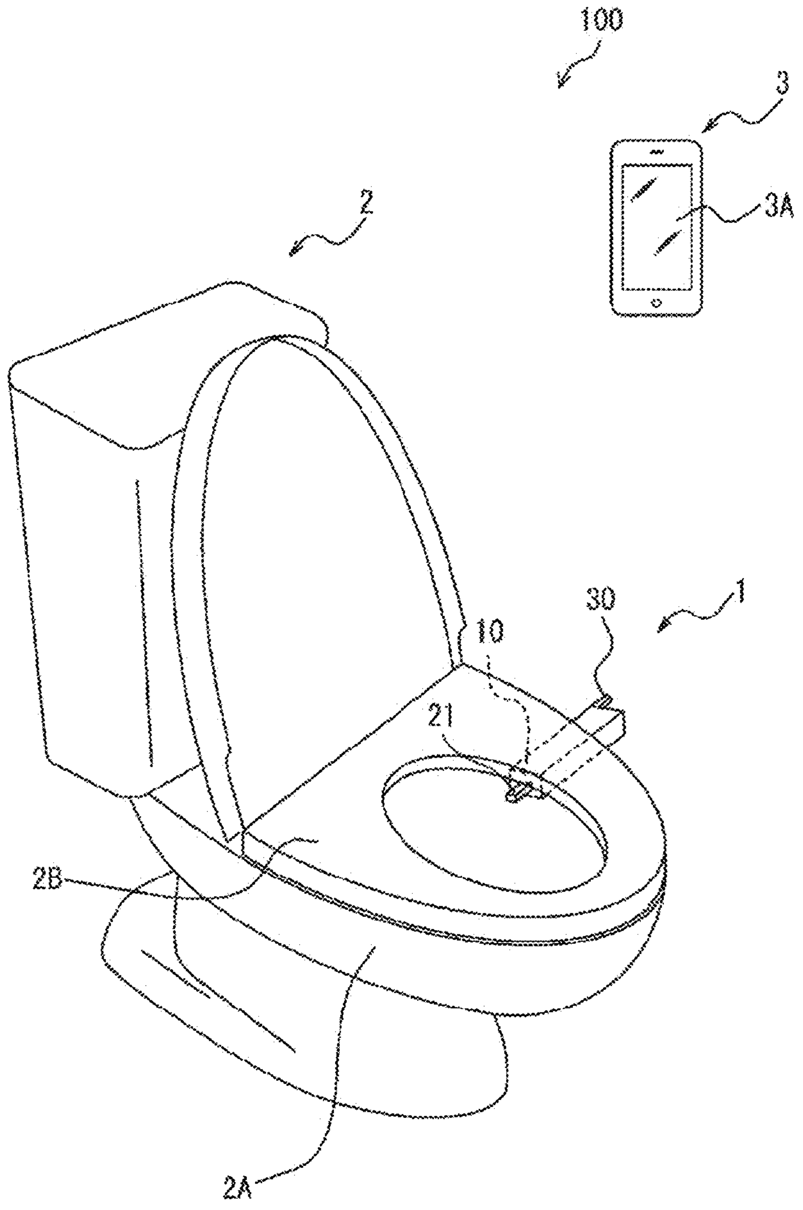
FIG. 1 is an external view illustrating an example of a configuration of an analysis system according to one embodiment of the present disclosure.

FIG. 1 is an external view illustrating a configuration of an example of an analysis system 100 according to one embodiment of the present disclosure. For convenience of explanation, drawings referred to this specification are schematic diagrams illustrating only some members in a simplified manner for describing the embodiments. Thus, the analysis system 100 may include any constituent members not illustrated in the drawings to which this specification refers. The dimensions of the members in the drawings do not faithfully represent the actual dimensions of the constituent members, the dimension ratios of the members, or the like.

The analysis system 100 as illustrated in FIG. 1 may be referred to as a "gas detection system" or a "gas analysis system". As illustrated in FIG. 1, the analysis system 100 includes a gas detection apparatus 1 and an electronic device (terminal device) 3. The gas detection apparatus 1 detects gas generated from a specimen from an examinee. The detected gas may be used for analysis of the health condition of the examinee or the like. Here, the specimen from the examinee which may be, for example, a part of a tissue, urine, or the like from the examinee, is feces from the examinee in the present embodiment. A chemical substance that is a target of detection by a gas sensor group 24 (described below) in the gas detection apparatus 1 and that can exist in a gaseous form is referred to as "detection target gas". The detection target gas may be of one type or of a plurality of types. The detection target gas may be in, for example, gas (sample gas) discharged from feces from the examinee. The concentration of the detection target gas means the concentration of the chemical substance to be detected in the sample gas.

As illustrated in FIG. 1, the gas detection apparatus 1 is provided to a flushing toilet 2, for example. The toilet 2 includes a toilet bowl 2A and a toilet seat 2B. The gas detection apparatus 1 may be provided at any position on the toilet 2. As an example, as illustrated in FIG. 1, the gas detection apparatus 1 may be disposed from a part between the toilet bowl 2A and the toilet seat 2B to the outside of the toilet 2. The gas detection apparatus 1 may be partially embedded in the toilet seat 2B. Feces from the examinee may be discharged into the toilet bowl 2A of the toilet 2. The gas detection apparatus 1 can acquire sample gas that is a mixture of gas emitted from feces discharged into the toilet bowl 2A and outside air. The gas detection apparatus 1 may detect a type, concentration, and the like of the detection target gas in the sample gas. The gas detection apparatus 1 can transmit a detection result to the electronic device 3.

The toilet 2 may be installed in a toilet room of a house, a hospital, or the like. The electronic device 3 is, for example, a smartphone used by the examinee. However, the electronic device 3 is not limited to a smartphone and may be any electronic device. The electronic device 3 may be located inside the toilet room or may be located outside the toilet room.

The electronic device 3 can receive the detection result from the gas detection apparatus 1 through wireless communications or wired communications. In this case, the electronic device 3 may receive the detection result from the gas detection apparatus 1 via a server. The electronic device 3 may display the received detection result on a displayer 3A. The displayer 3A may include a display capable of displaying characters and a touch screen capable of detecting contact of a user's (examinee's) finger. This display may include a display device such as a liquid crystal display (LCD), an organic electro-luminescence display (OELD), or an inorganic electro-luminescence display (IELD). A detection method of this touch screen may be any method such as a capacitive method, a resistive film method, a surface acoustic wave method, an ultrasonic method, an infrared method, an electromagnetic inductive method, or a load detection method.

<Gas Detection Apparatus 1>

Figure 2:
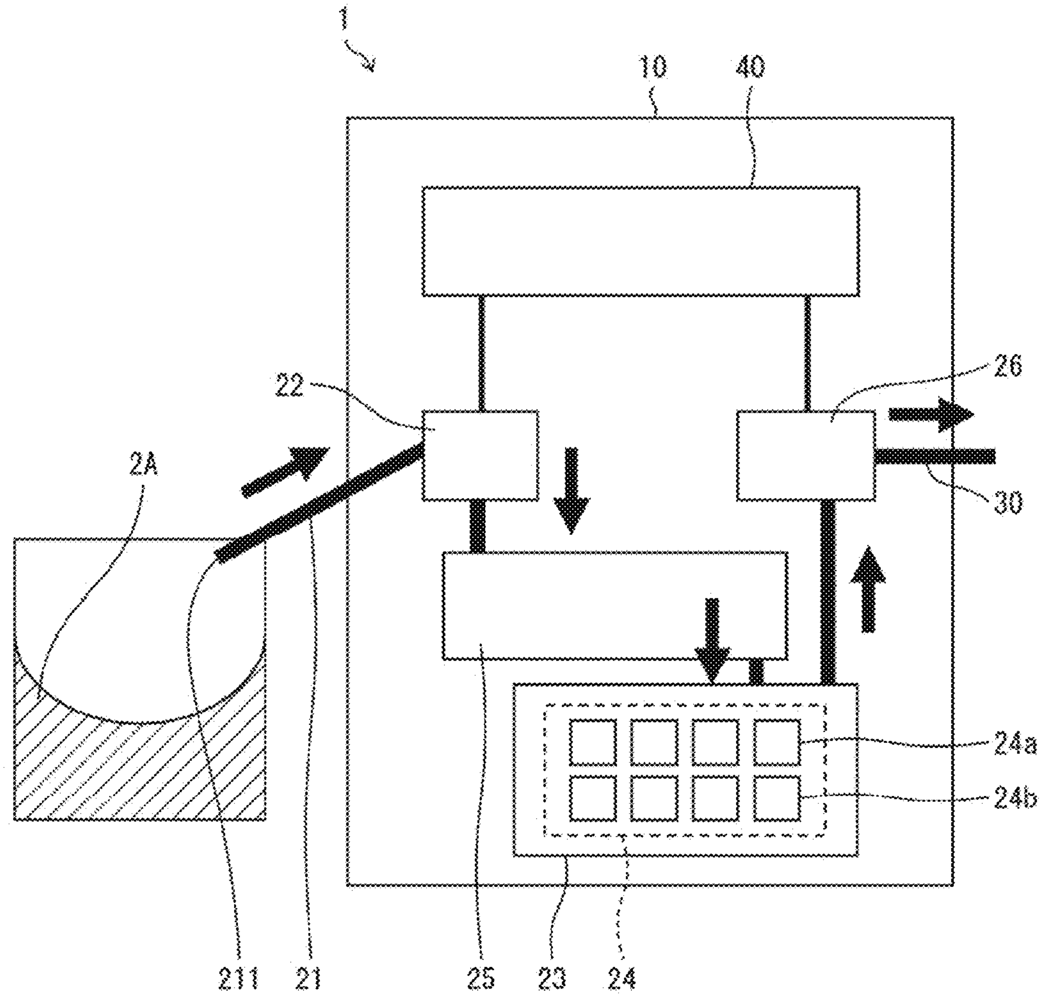
FIG. 2 is a schematic view illustrating an example of a configuration of a gas detection apparatus according to one embodiment of the present disclosure.
Figure 3:
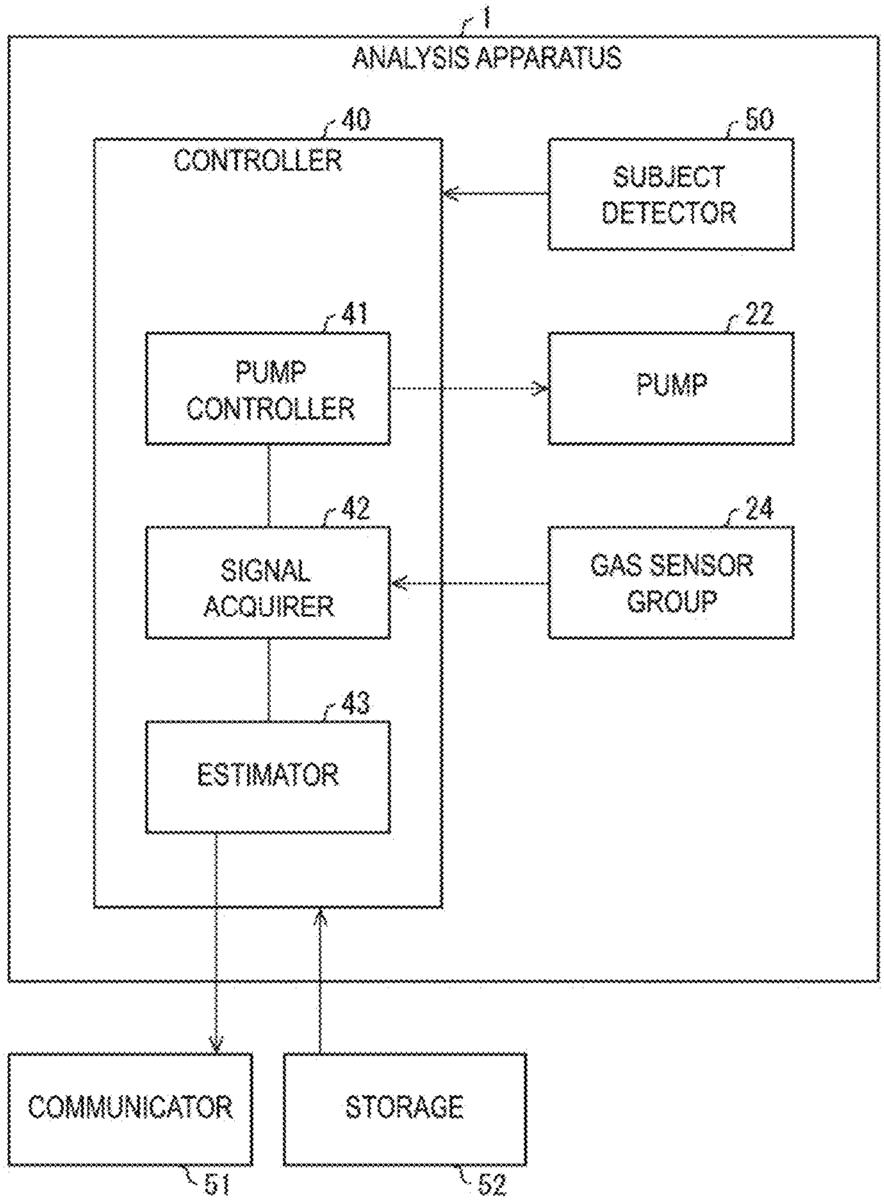
FIG. 3 is a block diagram illustrating an example of a configuration of the gas detection apparatus according to one embodiment of the present disclosure.

FIG. 2 is a schematic view illustrating an example of a configuration of the gas detection apparatus 1 according to one embodiment. FIG. 3 is a block diagram illustrating an example of a configuration of the gas detection apparatus 1. As described above, the gas detection apparatus 1 is installed in the toilet 2, collects the sample gas including gas discharged from the feces of the examinee, and can detect the type, the concentration, and the like of the detection target gas in the sample gas. The gas detection apparatus 1 can transmit information indicating the type, concentration, and the like of the detected detection target gas to the electronic device 3 as the detection result. As illustrated in FIGS. 2 and 3, the gas detection apparatus 1 includes a housing 10, a collector 21 (sample gas collector), a storage pump 22, a storage tank 25, a sensor chamber 23 (gas detector), the gas sensor group 24, a chamber pump 26, a discharge path 30, a controller 40, a subject detector 50, a communicator 51, and a storage 52.

(Housing 10)

The housing 10 accommodates various components of the gas detection apparatus 1. The housing 10 may be formed of any material. For example, the housing 10 may be made of a material such as metal or resin.

[Collector 21]

The collector 21 is a tubular member that collects the sample gas in a target space and supplies the collected sample gas into the storage tank 25. The collector 21 has an opening 211 exposed to the inside of the toilet bowl 2A and opened toward the inside of the toilet bowl 2A, and collects the sample gas in the toilet bowl 2A as the target space, through an operation of a storage pump 22 (described below). The collector 21 has a sample flow path through which the sample gas flows. Here, the sample flow path means a flow path through which the collected sample gas travels. The sample flow path establishes communication between the opening 211 and the sensor chamber 23.

[Storage Pump 22]

The storage pump 22 is a pump located on the sample flow path. The storage pump 22 may operate under the control by a pump controller 41 (described below). For example, the storage pump 22 may be a pump that operates at a constant air supply rate. The storage pump 22 may supply the sample gas from the collector 21 into the storage tank 25.

[Storage Tank 25]

The storage tank 25 is located behind the storage pump 22 on the sample flow path, and temporarily stores the sample gas collected from the collector 21 by the storage pump 22. However, the function of the storage tank 25 is not limited to the temporarily storage of the sample gas, and the storage tank 25 may function as a part of a flow path that does not store the sample gas. The storage tank 25 may be formed of resin to be in a bag shape, or may be formed of metal to be in a cylindrical shape or a rectangular shape.

[Sensor Chamber 23]

The sensor chamber 23 is a chamber that accommodates the gas sensor group 24 therein. The sensor chamber 23 is in communication with the storage tank 25. The number of gas sensors in the gas sensor group 24 accommodated in the sensor chamber 23 is not particularly limited. The gas sensor group 24 may include any number of gas sensors depending on the type and number of detection target gases.

[Gas Sensor Group 24]

The gas sensor group 24 includes a first gas sensor 24*a* and a second gas sensor 24*b*. Each of the first gas sensor 24*a* and the second gas sensor 24*b* is a gas sensor capable of detecting both the first detected gas and the second detected gas. Thus, the first detected gas and the second detected gas are the detection target gas of each of the first gas sensor 24*a* and the second gas sensor 24*b*. Hereinafter, the detection signal output from the first gas sensor 24*a* is referred to as a first detection signal. The detection signal output from the second gas sensor 24*b* will be referred to as a second detection signal.

The gas sensor group 24 may be a set of sensors that output different detection signals depending on the concentration of the detection target gas. In the following description, as a sensor constituting the gas sensor group 24, a sensor outputting a detection signal with the intensity changing in accordance with the concentration of the detection target gas will be described as an example, but the sensor is not limited thereto. As an example, the sensors constituting the gas sensor group 24 can output a detection signal with intensity corresponding to the concentration of the detection target gas that may be included in the sample gas, to a signal acquirer 42 of the controller 40. As illustrated in FIG. 2, the gas detection apparatus 1 may include a plurality of gas sensors. The plurality of gas sensors may be capable of outputting detection signals respectively corresponding to the concentrations of different types of the detection target gas. Thus, the gas detection apparatus 1 can analyze the concentrations of a plurality of types of the detection target gas.

Each of the first detected gas and the second detected gas may be a gas with a composition formula including a sulfur atom. A sensor that is sensitive to a certain kind of gas with a composition formula including a sulfur atom tends to be sensitive to another kind of gas with a composition formula including a sulfur atom. Therefore, when the sample gas includes a plurality of types of detection target gas each having a composition formula including a sulfur atom, it is difficult to detect the concentration of any one of the plurality of types of detection target gas with a single gas sensor. With the gas detection apparatus 1, instead of detecting the concentration of each of a plurality of types of detection target gas with a composition formula including a sulfur atom, the concentration can be accurately estimated based on the first detection signal and the second detection signal as will be described below.

Specifically, the first detected gas may be hydrogen sulfide. The second detected gas may be methyl mercaptan. Hydrogen sulfide and methyl mercaptan are gas species the concentration of each of which is particularly difficult to detect with a single gas sensor. With the gas detection apparatus 1, instead of detecting the concentration of each of hydrogen sulfide and methyl mercaptan, the concentration can be accurately estimated based on the first detection signal and the second detection signal as will be described below. Note that the first detected gas and the second detected gas may be gas with a composition formula including sulfur atom, which is different from hydrogen sulfide and methyl mercaptan.

The first detected gas and the second detected gas are not limited to gas with a composition formula including a sulfur atom. For example, each of the first detected gas and the second detected gas may be gas including a nitrogen atom. Also when the sample gas includes a plurality of types of detection target gas with a composition formula including a nitrogen atom, it is difficult to detect the concentration of any one of the plurality of types of detection target gas with a single gas sensor. With the gas detection apparatus 1, instead of detecting the concentration of each of a plurality of types of detection target gas with a composition formula including a nitrogen atom, the concentration can be accurately estimated based on the first detection signal and the second detection signal as will be described below.

Figure 4:
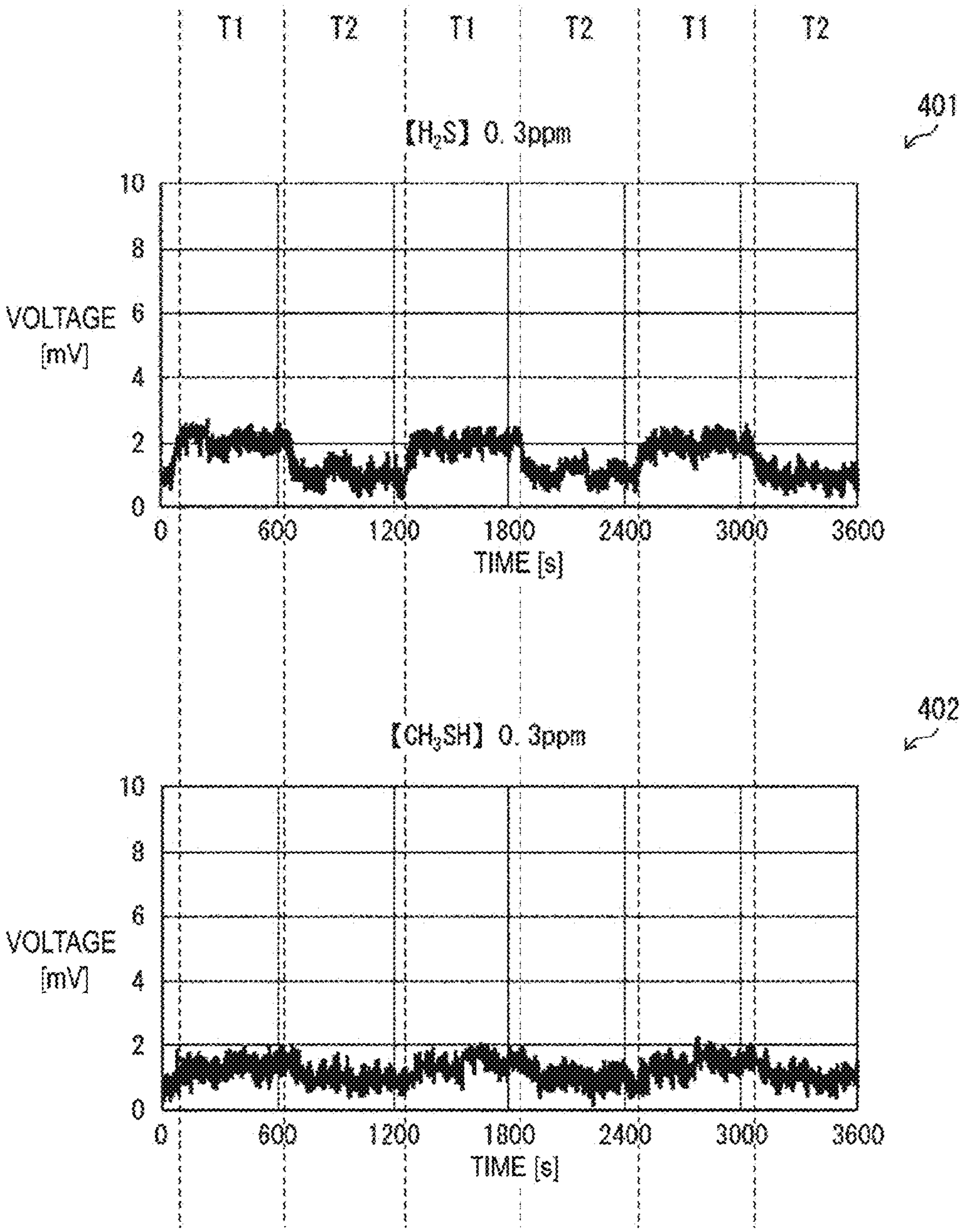
FIG. 4 is a graph illustrating an example of variation of a first detection signal attributable to hydrogen sulfide and methyl mercaptan.

FIG. 4 is a graph illustrating an example of variation of the first detection signal output from the first gas sensor 24*a*, attributable to hydrogen sulfide and methyl mercaptan. In FIG. 4, the horizontal axis represents time and the vertical axis represents the first detection signal (voltage). In FIG. 4, reference numeral 401 is a graph indicating an example of variation in the first detection signal, attributable to hydrogen sulfide the concentration of which is 0.3 ppm. In FIG. 4, reference numeral 402 is a graph indicating an example of variation in the first detection signal, attributable to methyl mercaptan the concentration of which is 0.3 ppm. A period T1 in FIG. 4 is a period during which hydrogen sulfide or methyl mercaptan is supplied to the first gas sensor 24*a*. A period T2 in FIG. 4 is a period during which the supply of hydrogen sulfide or methyl mercaptan to the first gas sensor 24*a* is stopped and the hydrogen sulfide or methyl mercaptan that has been supplied until then is removed using, for example, external air, nitrogen, or the like.

As indicated by reference numeral 401 in FIG. 4, clear variation in the first detection signal between the period T1 and the period T2 attributable to hydrogen sulfide can be observed. On the other hand, as indicated by reference numeral 402 in FIG. 4, slight variation in the first detection signal, attributable to methyl mercaptan, can be observed between the period T1 and the period T2, but this variation is smaller than the variation attributable to hydrogen sulfide. Thus, the detection sensitivity of the first gas sensor 24*a* to hydrogen sulfide is higher than the detection sensitivity to the detection sensitivity of the first gas sensor 24*a* to methyl mercaptan.

Figure 5:
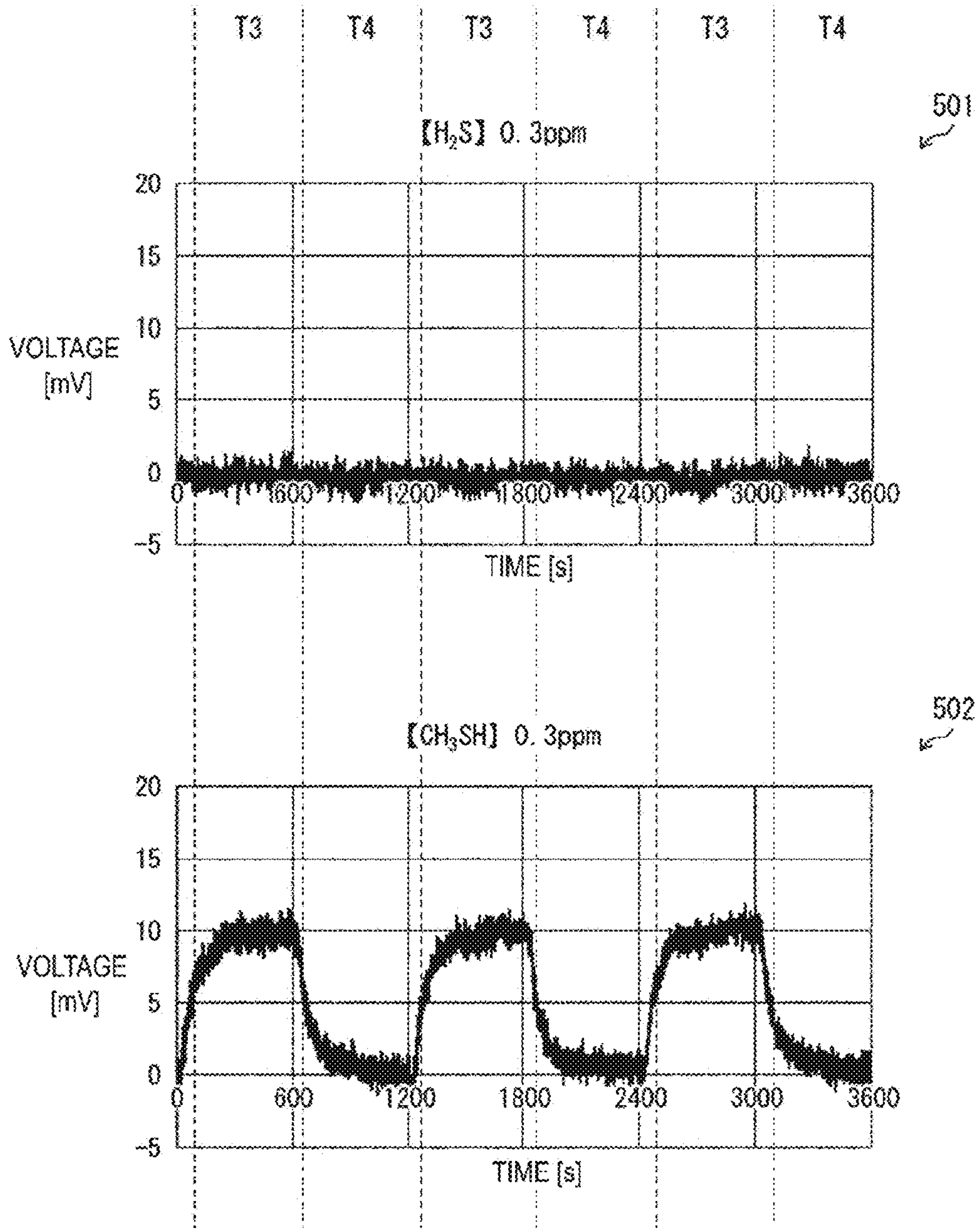
FIG. 5 is a graph illustrating an example of variation of a second detection signal attributable to hydrogen sulfide and methyl mercaptan.

FIG. 5 is a graph illustrating an example of variation in the second detection signal output from the second gas sensor 24*b*, attributable to hydrogen sulfide and methyl mercaptan. In FIG. 5, the horizontal axis represents time and the vertical axis represents the second detection signal (voltage). In FIG. 5, reference numeral 501 is a graph indicating an example of variation in the second detection signal, attributable to hydrogen sulfide the concentration of which is 0.3 ppm. In FIG. 5, reference numeral 502 is a graph indicating an example of variation in the second detection signal, attributable to methyl mercaptan the concentration of which is 0.3 ppm. A period T3 in FIG. 5 is a period during which hydrogen sulfide or methyl mercaptan is supplied to the second gas sensor 24*b*. A period T4 in FIG. 5 is a period during which the supply of hydrogen sulfide or methyl mercaptan to the first gas sensor 24*a* is stopped and the hydrogen sulfide or methyl mercaptan that has been supplied until then is removed using, for example, external air, nitrogen, or the like.

As indicated by reference numeral 502 in FIG. 5, clear variation in the second detection signal between the period T3 and the period T4 attributable to methyl mercaptan can be observed. On the other hand, as indicated by reference numeral 501 in FIG. 5, slight variation in the second detection signal, attributable to hydrogen sulfide, can be observed between the period T3 and the period T4, but this variation is smaller than the variation attributable to methyl mercaptan. Thus, the detection sensitivity of the second gas sensor 24*b* to methyl mercaptan is higher than the detection sensitivity of the second gas sensor 24*b* to hydrogen sulfide.

As illustrated in FIGS. 4 and 5, the first gas sensor 24*a* and the second gas sensor 24*b* may be different from each other in the relative relationship between the detection sensitivity to hydrogen sulfide and the detection sensitivity to methyl mercaptan. Specifically, when the concentrations of hydrogen sulfide and methyl mercaptan are the same, the ratio of the intensity of the first detection signal attributable to methyl mercaptan to the intensity of the first detection signal attributable to hydrogen sulfide may be lower than the ratio of the intensity of the second detection signal attributable to methyl mercaptan to the intensity of the second detection signal attributable to hydrogen sulfide. Since the gas sensor group 24 includes the first gas sensor 24*a* and the second gas sensor 24*b*, the concentrations of hydrogen sulfide and methyl mercaptan can be accurately estimated as will be described below.

[Chamber Pump 26]

The chamber pump 26 is a pump that introduces the sample gas from the storage tank 25 into the sensor chamber 23. The chamber pump 26 may operate under the control by the pump controller 41 (described below). For example, the chamber pump 26 may be a pump that operates at a constant air supply rate. The discharge amount of the chamber pump 26 may be set to be smaller than the discharge amount of the storage pump 22.

(Discharge Path 30)

The discharge path 30 may be configured by a tubular member such as a resin tube, or a metal or glass pipe. The discharge path 30 establishes communication between the sensor chamber 23 and the outside of the housing 10. The chamber pump 26 may be provided in the middle of the discharge path 30. The discharge path 30 discharges the exhaust gas from the sensor chamber 23 to the outside of the gas detection apparatus 1, through the operation of the chamber pump 26. The discharge path 30 may be partially exposed to the outside of the toilet bowl 2A as illustrated in FIG. 1.

(Controller 40)

The controller 40 controls the operation of each component of the gas detection apparatus 1 and estimates the concentration of the detection target gas in the sample gas. As illustrated in FIG. 3, the controller 40 includes the pump controller 41, the signal acquirer 42, and an estimator 43.

[Pump Controller 41]

The pump controller 41 controls operations of the storage pump 22 and the chamber pump 26. Specifically, the pump controller 41 operates the storage pump 22 and the chamber pump 26 in accordance with a result of detection by the subject detector 50 (described below), and stops the storage pump 22 and the chamber pump 26 after a predetermined time elapses. As a result, the sample gas in the toilet bowl 2A is sucked from the collector 21, and supplied to the sensor chamber 23 via the storage tank 25.

[Signal Acquirer 42]

The signal acquirer 42 acquires, from each gas sensor in the gas sensor group 24, a detection signal corresponding to the type and concentration of the detection target gas in the sample gas. Specifically, the signal acquirer 42 may acquire the detection signal output from each gas sensor in the gas sensor group 24, when the operation of the storage pump 22 and the chamber pump 26 by the pump controller 41 stops.

[Estimator 43]

The estimator 43 estimates the type and concentration of the detection target gas in the sample gas based on the detection signal acquired by the signal acquirer 42 from each gas sensor in the gas sensor group 24. The detection signal acquired from each gas sensor is a detection signal output from the gas sensor. The estimator 43 may estimate the concentrations of the first detected gas and the second detected gas based on the first detection signal output from the first gas sensor 24*a* and the second detection signal output from the second gas sensor 24*b*. As described above, the first gas sensor 24*a* and the second gas sensor 24*b* are each capable of detecting both the first detected gas and the second detected gas. Therefore, the combination of the concentration of the first detected gas and the second detected gas cannot be uniquely estimated based on only one of the first detection signal and the second detection signal. As described above, the first gas sensor 24*a* and the second gas sensor 24*b* are different from each other in the relative relationship between the detection sensitivity to the first detected gas and the detection sensitivity to the second detected gas. Thus, the estimator 43 can uniquely estimate the combination of the concentration of the first detected gas and the concentration of the second detected gas that matches both the first detection signal and the second detection signal.

As illustrated in FIG. 3, the estimator 43 may be provided in the controller 40 of the gas detection apparatus 1. The estimator 43 may not be provided in the controller 40 but may be provided on a cloud connected to the gas detection apparatus 1 via a network. When the estimator 43 is provided on the cloud, the signal acquirer 42 may transmit the detection signal acquired from each gas sensor in the gas sensor group 24, to the cloud via the network. The estimator 43 on the cloud may estimate the type and the concentration of the detection target gas based on the detection signal transmitted from the signal acquirer 42.

The estimator 43 may estimate the concentrations of the first detected gas and the second detected gas in the sample gas using a concentration estimation model created from the first detection signal and the second detection signal for a plurality of types of teacher gas. The teacher gas is sample gas including the first detected gas and the second detected gas whose concentrations are known. The concentration estimation model may be created by machine learning using a set of the first detection signal and the second detection signal for the teacher gas and the concentrations of the first detected gas and the second detected gas in the teacher gas. The estimator 43 can easily perform the estimation by estimating the concentrations of the first detected gas and the second detected gas using such a concentration estimation model.

(Subject Detector 50)

The subject detector 50 may include at least one of an image camera, an individual identification switch, an infrared sensing device, and a pressure sensing device (not illustrated). The subject detector 50 outputs a detection result to the controller 40.

For example, when the subject detector 50 includes an infrared sensing device, the infrared sensing device can detect that the examinee has entered the toilet room by emitting infrared light and detecting the light reflected from an object. The subject detector 50 outputs a signal indicating that the examinee has entered the toilet room to the controller 40 as a detection result.

For example, when the subject detector 50 includes a pressure sensing device, the subject detector 50 can detect that the examinee has sat on the toilet seat 2B by detecting pressure applied to the toilet seat 2B as illustrated in FIG. 1. The subject detector 50 outputs a signal indicating that the examinee has sat on the toilet seat 2B to the controller 40 as a detection result.

For example, when the subject detector 50 includes a pressure sensing device, the subject detector 50 can detect that the examinee has stood up from the toilet seat 2B by detecting a decrease in pressure applied to the toilet seat 2B as illustrated in FIG. 1. The subject detector 50 outputs a signal indicating that the examinee has stood up from the toilet seat 2B to the controller 40 as a detection result.

For example, when the subject detector 50 includes an image camera and an individual identification switch, the subject detector 50 collects data such as a face image, sitting height, and weight. The subject detector 50 specifies/identifies from the collected data and detects an individual. The subject detector 50 outputs a signal indicating the specified/identified individual to the controller 40 as a detection result.

For example, when the subject detector 50 includes an individual identification switch, the subject detector 50 specifies (detects) an individual based on operation of the individual identification switch. In this case, personal information may be registered (stored) in advance in the storage 52. The subject detector 50 outputs a signal indicating the specified individual to the controller 40 as a detection result.

The subject detector 50 may detect that the examinee has defecated. The subject detector 50 outputs a signal indicating that the examinee has defecated to the controller 40 as a detection result.

(Communicator 51)

The communicator 51 communicates with the electronic device 3 that presents a result of the analysis on the detection target gas by the controller 40 to the examinee by, for example, display on the displayer 3A or voice. The communicator 51 may be capable of communicating with an external server. A communication method used in communication between the communicator 51 and the electronic device 3 and the external server may be a short-range wireless communication standard, a wireless communication standard for connection to a mobile phone network, or a wired communication standard. The short-range wireless communication standard may include, for example, WiFi (registered trademark), Bluetooth (registered trademark), infrared rays, and near field communication (NFC). The wireless communication standard for connection to the mobile phone network may include, for example, Long Term Evolution (LTE), or a fourth generation or higher mobile communication system. The communication method used in communication between the communicator 51 and the electronic device 3 and the external server may be a communication standard such as low power wide area (LPWA) or low power wide area network (LPWAN) for example.

(Storage 52)

The storage 52 may be, for example, a semiconductor memory, a magnetic memory, or the like. The storage 52 stores various kinds of information and programs for operating the gas detection apparatus 1. The storage 52 may function as a work memory. The storage 52 may store, for example, the concentration estimation model for the estimator 43 to estimate the concentrations of the first detected gas and the second detected gas.

<Effects of Gas Detection Apparatus 1>

An accurate concentration has not been measurable by a single sensor depending on the kind of the detection target gas. In view of this, the gas detection apparatus 1 may include the collector 21, the storage pump 22, the storage tank 25, the sensor chamber 23, the gas sensor group 24, the chamber pump 26, and the controller 40. In particular, the gas sensor group 24 may include the first gas sensor 24*a* and the second gas sensor 24*b*. The controller 40 may include the estimator 43.

With to the above-described configuration, in the gas detection apparatus 1, the concentration of the detection target gas in the sample gas is detected by the gas sensor group 24 including the first gas sensor 24*a* and the second gas sensor 24*b*. Each of the first gas sensor 24*a* and the second gas sensor 24*b* may be a gas sensor capable of detecting both the first detected gas and the second detected gas. Based on the first detection signal output by the first gas sensor 24*a* and the second detection signal output by the second gas sensor 24*b*, the estimator 43 estimates the concentrations of the first detected gas and the second detected gas. As a result, the gas detection apparatus 1 can estimate the concentration with high accuracy for gas whose concentration is difficult to accurately measure by a single sensor.

Second Embodiment

Another embodiment of the present disclosure will be described below. For the sake of convenience of description, members having the same functions as those of the members described in the above-described embodiment are denoted by the same reference signs, and description thereof is not repeated.

In the gas detection apparatus 1, each of the first gas sensor 24*a* and the second gas sensor 24*b* may be an electrochemical sensor. When the first gas sensor 24*a* and the second gas sensor 24*b* are electrochemical sensors, the concentrations of the first detected gas and the second detected gas described above can be detected with high sensitivity.

In the gas detection apparatus 1, the first gas sensor 24*a* and the second gas sensor 24*b* are not limited to electrochemical sensors, and may be, for example, semiconductor-type sensors, quartz crystal microbalance (QCM) sensors, complementary metal oxide semiconductor (CMOS)-type sensors, sensitive film-type sensors, optical sensors, photoacoustic sensors, or the like. As the sensitive film type sensor, a sensitive film stress type sensor, a sensitive film resonance type sensor, or the like may be used. The gas sensor group 24 may include a plurality of types of sensors. The first gas sensor 24*a* and the second gas sensor 24*b* may be selected in accordance with the first detected gas and the second detected gas which are detection targets.

Figure 6:
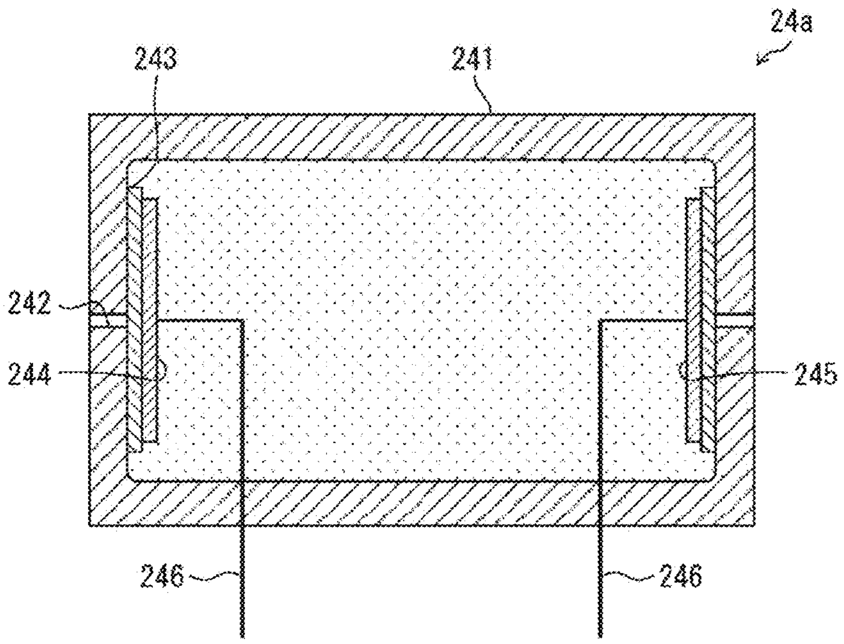
FIG. 6 is a partial cross-sectional view illustrating an example of a configuration of a first gas sensor in a gas sensor group.

FIG. 6 is a partial cross-sectional view illustrating an example of a configuration of the first gas sensor 24*a* in the gas sensor group 24. The second gas sensor 24*b* may have the same configuration as the first gas sensor 24*a*, and thus is not illustrated. As illustrated in FIG. 6, the first gas sensor 24*a* may include a case 241, a first electrode 244, a second electrode 245, and an electrode pin 246.

The case 241 is a housing that accommodates the first electrode 244 (electrode), the second electrode 245 (electrode), and an electrolytic solution. There may be a reference electrode between the first electrode 244 and the second electrode 245. In the case 241, a vent hole 242 for taking in the sample gas is formed. The vent hole 242 may be provided with a prefilter 243 for suppressing the entry of foreign matter such as dust into the case 241.

The first electrode 244 and the second electrode 245 may be disposed at positions opposite to each other in the case 241, for example. The first electrode 244 may be disposed, for example, on the vent hole 242 side. In this case, the second electrode 245 may be provided, for example, on the side of a surface opposite to the first electrode 244 in the case 241. When the first electrode 244 and the second electrode 245 are adjacent to each other, a nonwoven fabric may be disposed therebetween.

In the first gas sensor 24*a*, the first electrode 244 and the second electrode 245 are electrically connected to each other via the electrolytic solution. The first electrode 244, the second electrode 245, and the electrolytic solution constitute an electrode unit that outputs a signal corresponding to the concentration of the detection target gas in the sample gas. The first electrode 244 and the second electrode 245 may be electrodes containing carbon as a main component. The electrolytic solution may contain, for example, sulfuric acid as a main component, but is not limited thereto.

When the sample gas taken into the case 241 through the vent hole 242 comes into contact with the electrolytic solution, a part of the sample gas is dissolved in the electrolytic solution, and the resistance value between the first electrode 244 and the second electrode 245 changes. The degree of change in resistance value varies depending on the type and concentration of the gas in the sample gas. As a result, the voltage between the first electrode 244 and the second electrode 245 changes according to the type and concentration of the gas in the sample gas. The change in the voltage serves as a signal indicating the type and concentration of the gas in the sample gas.

The electrode pin 246 is a pin for extracting the signals output from the first electrode 244 and the second electrode 245 to the outside. The first gas sensor 24*a* may include the electrode pin 246 connected to the first electrode 244 and the electrode pin 246 connected to the second electrode 245. The electrode pin 246 may be formed of, for example, platinum, but is not limited thereto.

Third Embodiment

Yet another embodiment of the present disclosure will be described below.

Figure 7:
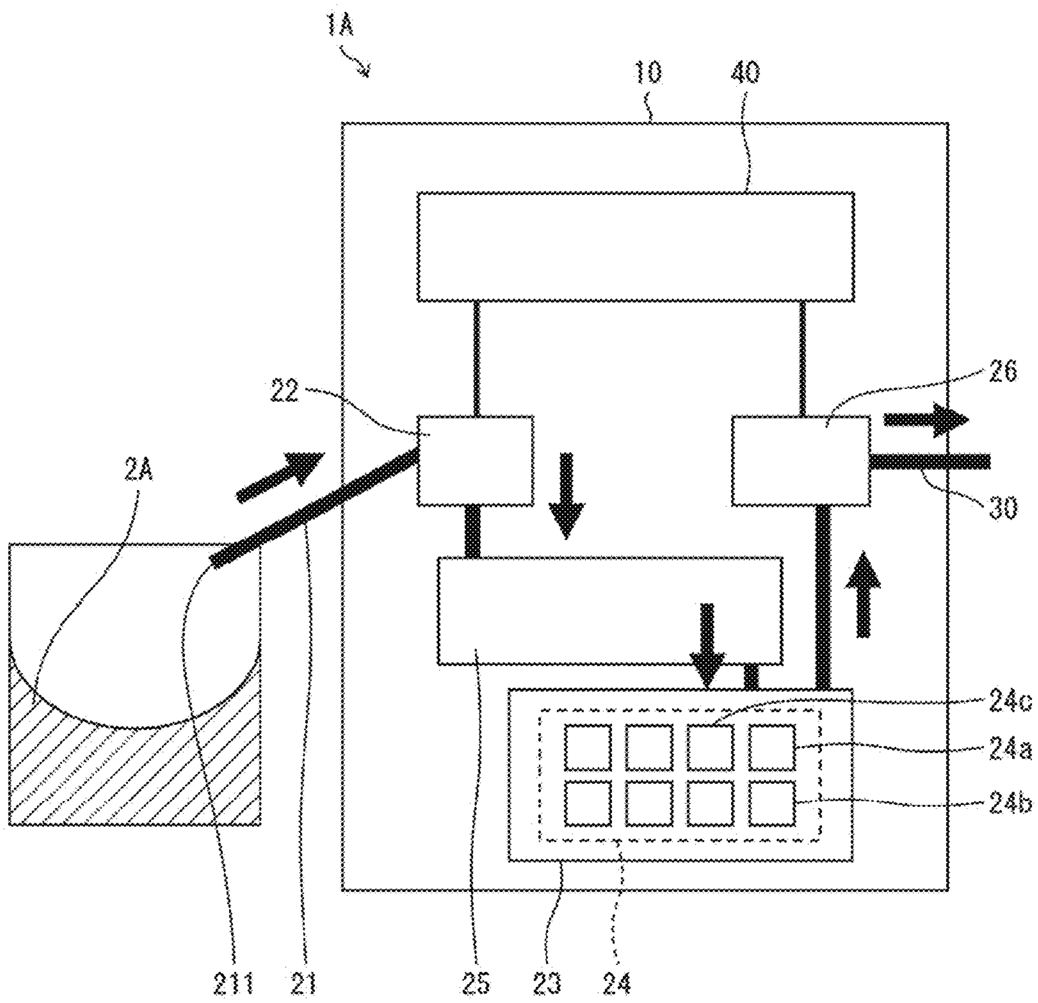
FIG. 7 is a schematic view illustrating an example of a configuration of a gas detection apparatus according to a third embodiment.

FIG. 7 is a schematic view illustrating an example of a configuration of a gas detection apparatus 1A according to a third embodiment. As illustrated in FIG. 7, the gas detection apparatus 1A differs from the gas detection apparatus 1 only in that the gas sensor group 24 further includes a third gas sensor 24*c*.

The third gas sensor 24*c* is a gas sensor capable of detecting the first detected gas and the second detected gas. The detection sensitivity of the third gas sensor 24*c* to the first detected gas may be different from both the detection sensitivity of the first gas sensor 24*a* to the first detected gas and the detection sensitivity of the second gas sensor 24*b* to the first detected gas. Since the gas detection apparatus 1A includes the third gas sensor 24*c*, three types of detection signals for the first detected gas and the second detected gas can be obtained. Therefore, the concentrations of the first detected gas and the second detected gas can be estimated with higher accuracy.

Fourth Embodiment

Yet another embodiment of the present disclosure will be described below.

In the fourth embodiment, the first detected gas and the second detected gas are of gas species different from those in the first embodiment. In the fourth embodiment, the first detected gas may be hydrogen sulfide or methyl mercaptan. The second detected gas may be hydrogen, water, ammonia, or alcohol.

The second detected gas described above is gas that becomes noise in or interferes with an output signal from the gas sensor that detects the first detected gas. Thus, the concentration of the second detected gas affects the detection signal from the gas sensor that detects the first detected gas. Therefore, it is difficult to detect the concentration of the first detected gas with a single gas sensor in an environment including the second detected gas described above.

In the fourth embodiment, when the concentrations of the first detected gas and the second detected gas are the same, the ratio of the intensity of the second detection signal attributable to the second detected gas to the intensity of the second detection signal attributable to the first detected gas may be larger than 1. When the concentrations of the first detected gas and the second detected gas are substantially the same, the ratio of the intensity of the second detection signal attributable to the second detected gas to the intensity of the second detection signal attributable to the first detected gas may be larger than 10. Thus, the second gas sensor 24*b* may be a gas sensor that mainly detects the second detected gas. Since the gas detection apparatus 1 includes such a second gas sensor 24*b*, the estimator 43 can accurately estimate the concentration of the second detected gas based on the second detection signal. Thus, the estimator 43 can also accurately estimate the magnitude of the influence of the concentration of the second detected gas on the first detection signal. Therefore, the estimator 43 can accurately estimate the concentration of the first detected gas based on the first detection signal.

In the fourth embodiment, the influence of the second detection signal output from the second gas sensor 24*b* on the estimation of the concentration of the first detected gas is small. In general, such a second detection signal does not serve as an explanatory variable in the concentration estimation model for the first detected gas.

However, in machine learning for creating the concentration estimation model for estimation by the estimator 43, the second detection signal may also serve as an explanatory variable in the concentration estimation model for the first detected gas. With the second detection signal serving as the explanatory variable in the concentration estimation model for the first detected gas, the influence of the concentration of the second detected gas on the first detection signal can be reduced and the concentration of the first detected gas can be accurately estimated.

Fifth Embodiment

Yet another embodiment of the present disclosure will be described below.

Figure 8:
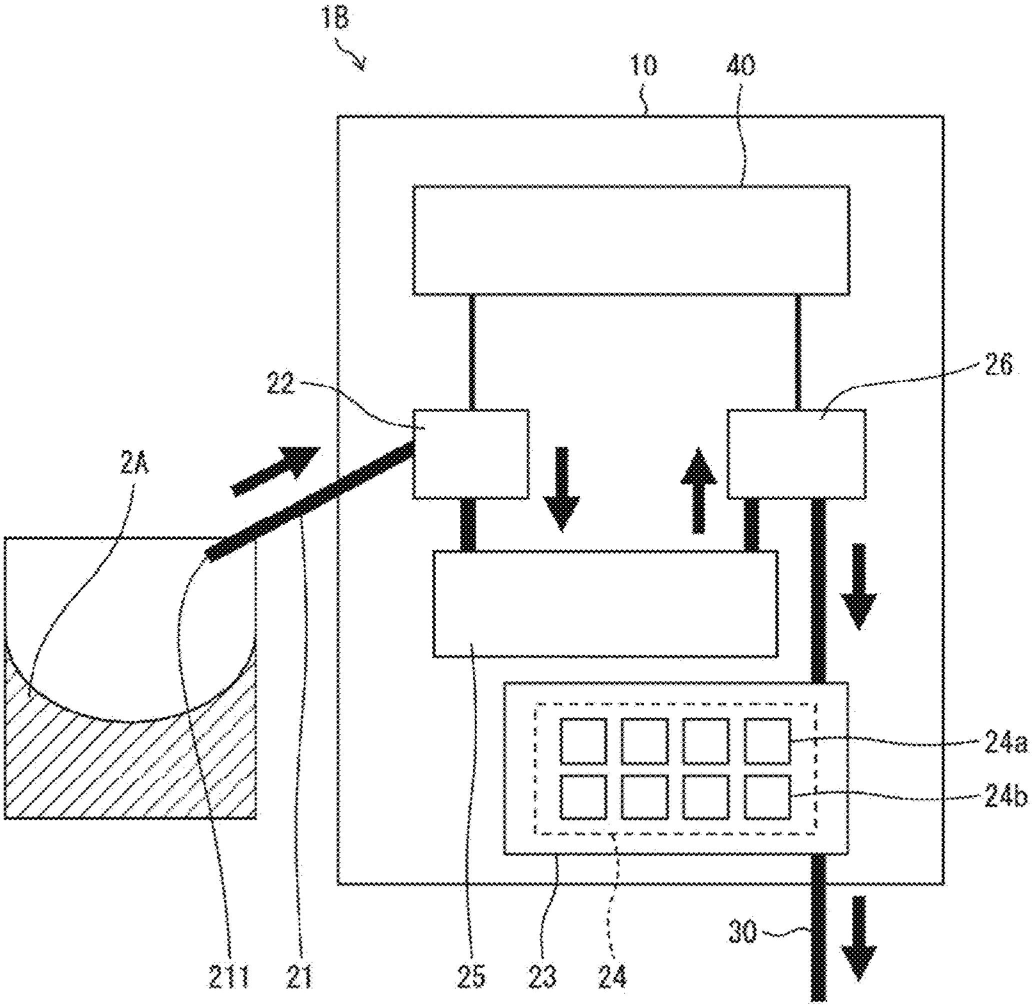
FIG. 8 is a schematic view illustrating an example of a configuration of a gas detection apparatus according to a fifth embodiment.

FIG. 8 is a schematic view illustrating an example of a configuration of a gas detection apparatus 1B according to a fifth embodiment. As illustrated in FIG. 8, the gas detection apparatus 1B is different from the gas detection apparatus 1 in that the sensor chamber 23 is located downstream of the chamber pump 26. Such a gas detection apparatus 1B can also estimate the concentration with high accuracy for gas whose concentration is difficult to accurately measure by a single sensor.

Example of Software Implementation

Functions of the gas detection apparatus 1, 1A, 1B (hereinafter, referred to as "apparatus") can be implemented by a program for causing a computer to function as the apparatus and for causing the computer to function as each control block (particularly, each unit in the controller 40) of the apparatus.

In this case, the apparatus includes a computer including at least one control device (for example, processor) and at least one storage device (for example, memory) as hardware for executing the program. By executing the program by the control device and the storage device, the functions described in the embodiments are implemented.

The program may be recorded on one or a plurality of computer-readable non-transitory recording media. The recording media may be or need not be in the apparatus. In the latter case, the program may be supplied to the apparatus via any wired or wireless transmission medium.

Some or all of the functions of the control blocks can be implemented by logic circuits. For example, an integrated circuit in which logic circuits functioning as the control blocks are formed is also in the scope of the present disclosure. In addition to this, for example, a quantum computer can implement the functions of the control blocks.

The several types of processing described in the embodiments may be executed by artificial intelligence (AI). In this case, the AI may operate in the control device, or may operate in another device (such as, for example, an edge computer or a cloud server).

The present disclosure is not limited to each of the embodiments described above, and various modifications can be made within the scope indicated by the claims, and an embodiment obtained by appropriately combining technical means disclosed in different embodiments is also in a technical scope of the present disclosure.

REFERENCE SIGNS

1, 1A, 1B Gas detection apparatus
21 Collector (sample gas collector)
23 Sensor chamber (gas detector)
24*a* First gas sensor
24*b* Second gas sensor
24*c* Third gas sensor
244 First electrode (electrode)
245 Second electrode (electrode)
43 Estimator

The invention claimed is:

1. A gas detection apparatus, comprising:
- a sample gas collector configured to collect sample gas containing first detected gas and second detected gas;
- a gas detector comprising a plurality of gas sensors comprising a first gas sensor and a second gas sensor capable of detecting both the first detected gas and the second detected gas contained in the sample gas;
- a storage tank configured to temporarily store the sample gas;
- a storage pump configured to supply the sample gas from the sample gas collector into the storage tank; and
- a chamber pump configured to introduce the sample gas from the storage tank into the gas detector, wherein
- the first gas sensor and the second gas sensor are different from each other in relative relationship between detection sensitivity to the first detected gas and detection sensitivity to the second detected gas;
- the storage pump is located upstream of the gas detector,
- the chamber pump is located downstream of the gas detector, and
- a discharge amount of the chamber pump is set to be smaller than a discharge amount of the storage pump.

2. The gas detection apparatus according to claim 1, wherein a ratio of intensity of a first detection signal attributable to the second detected gas to intensity of the first detection signal attributable to the first detected gas, the first detection signal being output from the first gas sensor, is lower than a ratio of intensity of a second detection signal attributable to the second detected gas to intensity of the second detection signal attributable to the first detected gas, the second detected signal being output from the second gas sensor.

3. The gas detection apparatus according to claim 1, wherein the first gas sensor and the second gas sensor are both an electrochemical sensor.

4. The gas detection apparatus according to claim 1, wherein the first detected gas and the second detected gas are both a gas containing a sulfur atom or both a gas containing a nitrogen atom in a composition formula.

5. The gas detection apparatus according to claim 4, wherein the first detected gas is hydrogen sulfide, and the second detected gas is methyl mercaptan.

6. The gas detection apparatus according to claim 3, wherein the gas detector further comprises a third gas sensor capable of detecting the first detected gas and the second detected gas, and detection sensitivity of the third gas sensor to the first detected gas is different from both the detection sensitivity of the first gas sensor to the first detected gas and the detection sensitivity of the second gas sensor to the first detected gas.

7. The gas detection apparatus according to claim 1, wherein the first detected gas is hydrogen sulfide or methyl mercaptan, the second detected gas is hydrogen, water, ammonia, or alcohol, and a ratio of the intensity of a second detection signal attributable to the second detected gas to the intensity of the second detection signal attributable to the first detected gas, the second detection signal being output from the second gas sensor, is larger than 1.

8. A gas detection system comprising:

a gas detection apparatus comprising:

a sample gas collector configured to collect sample gas containing first detected gas and second detected gas, a gas detector comprising a plurality of gas sensors comprising a first gas sensor and a second gas sensor capable of detecting both the first detected gas and the second detected gas contained in the sample gas, wherein the first gas sensor and the second gas sensor are different from each other in relative relationship between detection sensitivity to the first detected gas and detection sensitivity to the second detected gas;

a storage tank configured to temporarily store the sample gas;

a storage pump configured to supply the sample gas from the sample gas collector into the storage tank; and a chamber pump configured to introduce the sample gas from the storage tank into the gas detector, wherein the storage pump is located upstream of the gas detector, the chamber pump is located downstream of the gas detector, and a discharge amount of the chamber pump is set to be smaller than a discharge amount of the storage pump; and an estimator configured to estimate concentrations of the first detected gas and the second detected gas, based on a first detection signal output from the first gas sensor and a second detection signal output from the second gas sensor.

9. The gas detection system according to claim 8, wherein the estimator estimates the concentrations of the first detected gas and the second detected gas contained in the sample gas by using a concentration estimation model created from the first detection signal and the second detection signal for a plurality of types of teacher gas containing the first detected gas and the second detected gas whose concentrations are known.

10. The gas detection apparatus according to claim 1, further comprising:

a storage tank which is located between the sample gas collector and the gas detector and in which the sample gas is stored; and a storage pump which is located between the sample gas collector and the storage tank and which supplies the sample gas into the storage tank.

* * * * *